United States Patent

Dixon et al.

Patent Number: 5,932,577
Date of Patent: Aug. 3, 1999

[54] SUBSTITUTED OXOBUTYRIC ACIDS AS MATRIX METALLOPROTEASE INHIBITORS

[75] Inventors: Brian R. Dixon, Woodbridge; Jinshan Chen, Hamden; Michael C. VanZandt, Guilford; David R. Brittelli, Branford, all of Conn.

[73] Assignee: Bayer Corporation, Pittsburgh, Pa.

[21] Appl. No.: 08/857,053

[22] Filed: May 15, 1997

Related U.S. Application Data

[63] Continuation of application No. 08/648,384, May 15, 1996, abandoned
[60] Provisional application No. 60/051,007, May 15, 1996.
[51] Int. Cl.⁶ .................. A61K 31/53; C07D 251/00; C07D 209/48; C07C 65/32
[52] U.S. Cl. .................. 514/241; 514/417; 514/570; 544/220; 548/473; 562/459; 562/463
[58] Field of Search .................. 514/241, 417, 514/570; 544/220; 548/473; 562/459, 463

[56] References Cited

FOREIGN PATENT DOCUMENTS 9519961  7/1995  WIPO .................. C07C 323/41

OTHER PUBLICATIONS

Sahoo, et al., Inhibition of Matrix Metalloproteinases by N–Carboxyalkyl Dipeptides: Enhanced Potency and Selectivity with Substituted $P_1$' Homophenylanines, Biorganic & Medicinal Chemistry Letters, 5(20), 2441–2446 (1995).

Child, et al., Fenbufen, a New Anti–Inflammatory Analgesic: Synthesis and Structure–Activity Relationships of Analogs, Journal of Pharmaceutical Sciences, 66(4), 466–476 (1977).

*Primary Examiner*—Gary Geist
*Assistant Examiner*—Rosalynd Keys

[57] ABSTRACT

The present invention provides pharmaceutical compositions and methods for treating certain conditions associated with matrix metalloproteases comprising administering an amount of a compound or composition of the invention which is effective to inhibit the activity of at least one matrix metalloprotease, resulting in achievement of the desired effect. The compounds of the present invention are either of the generalized formula:

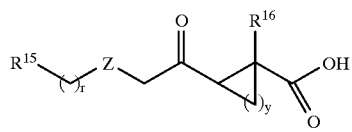

wherein y is 0, 2, or, 3, r is 0–6, Z is $(CH_2)_7$ or $(CH_2)_e$—$C_6H_4$—$(CH_2)_f$, wherein e is 0–1 and f is 0–5, and $R^{15}$ is —H, —Cl, —OMe or

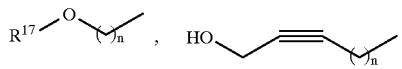

wherein n is 0–4, $R^{17}$ is $C_2H_5$, alkyl, benzyl, and $R^{16}$ is

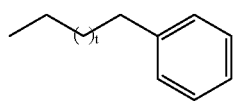

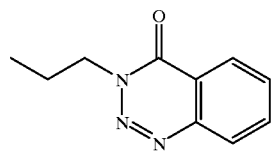

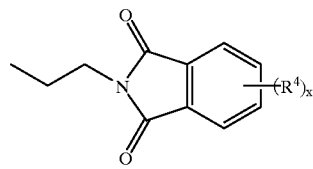

wherein t is 0–2, x is 0–4, and $R^4$ is one of the following: halide, alkyl of 1–6 carbons, OR, $NR_2$, $NO_2$ (R=H or alkyl of 1–6 carbons).

7 Claims, No Drawings

SUBSTITUTED OXOBUTYRIC ACIDS AS MATRIX METALLOPROTEASE INHIBITORS

This Application is a con of U.S. Ser. No. 08/648,384 filed May 15, 1996, ABN, which was converted to U.S. Provisional Appl. 60/051,007, filed May 15, 1996.

BACKGROUND OF THE INVENTION

1. Field of the Invention

This invention relates to enzyme inhibitors, and more particularly, to novel oxobutyric acids compounds or derivatives thereof useful for inhibiting matrix metalloproteases.

2. Description of the Related Art

The matrix metalloproteases (a.k.a. matrix metalloendoproteinases or MMPs) are a family of zinc endoproteinases which include, but are not limited to, interstitial collagenase (a.k.a. MMP-1), stromelysin (a.k.a.. proteoglycanase, transin, or MMP-3), gelatinase A (a.k.a.. 72 kDa-gelatinase or MMP-2) and gelatinase B (a.k.a.. 95 kDa-gelatinase or MMP-9). These MMPs are secreted by a variety of cells including fibroblasts and chondrocytes, along with natural proteinaceous inhibitors known as TIMPs (Tissue Inhibitor of MetalloProteinase)

All of these MMPs are capable of destroying a variety of connective tissue components of articular cartilage or basement membranes. Each MMP is secreted as an inactive proenzyme which must be cleaved in a subsequent step before it is able to exert its own proteolytic activity. In addition to the matrix destroying effect, certain of these MMPs such as MMP-3 have been implemented as the in vivo activator for other MMPs such as MMP-1 and MMP-9 (Ito, et al., Arch Biochem Biophys. 267, 211 (1988); Ogata, et al., J. Biol. Chem., 267, 3581 (1992)). Thus, a cascade of proteolytic activity can be initiated by an excess of MMP-3. It follows that specific MMP-3 inhibitors should limit the activity of other MMPs that are not directly inhibited by such inhibitors.

It has also been reported that MMP-3 can cleave and thereby inactivate the endogenous inhibitors of other proteinases such as elastase (Winyard, et al., FEBS Letts. 279, 1, 91 (1991)). Inhibitors of MMP-3 could thus influence the activity of other destructive proteinases by modifying the level of their endogenous inhibitors.

A number of diseases are thought to be mediated by excess or undesired matrix-destroying metalloprotease activity or by an imbalance in the ratio of the MMPs to the TIMPs. These include: a) osteoarthritis (Woessner, et al., J. Biol. Chem., 259(6), 3633 (1984); Phadke, et al., J. Rheumatol. 10, 852 (1983)), b) rheumatoid arthritis (Mullins, et al., Biochim. Biophys. Acta 695, 117 (1983); Woolley, et al., Arthritis Rheum. 20, 1231 (1977); Gravallese, et al., Arthritis Rheum. 34, 1076 (1991)), c) septic arthritis (Williams, et al., Arthritis Rheum. 33, 533 (1990)), d) tumor metastasis (Reich, et al., Cancer Res., 48, 3307 (1988); and Matrisian, et al., Proc. Nat'l. Acad. Sci., USA 83, 9413 (1986)), e) periodontal diseases (Overall, et al., J. Periodontal Res. 22, 81 (1987)), f) corneal ulceration (Burns, et al., Invest. Opthalmol. Vis. Sci. 30 1569 (1989)), g) proteinuria (Baricos, et al., Biochem. J. 254, 609 (1988)), h) coronary thrombosis from atherosclerotic plaque rupture (Henney, et al., Proc. Nat'l. Acad. Sci., USA 88, 8154 (1991)), i) aneurysmal aortic disease (Vine, et al., Clin. Sci. 81, 233 (1991)), j) birth control (Woessner, et al., Steroids 54, 491 (1989)), k) dystrophobic epidermolysis bullosa (Kronberger, et al., J. Invest. Dermatol. 79, 208 (1982)), and 1) degenerative cartilage loss following traumatic joint injury, m) conditions leading to inflammatory responses, osteopenias mediated by MMP activity, n) tempero mandibular joint disease, o) demyelating diseases of the nervous system (Chantry, et al., J. Neurochem. 50, 688 (1988)).

The need for new therapies is especially important in the case of arthritic diseases. The primary disabling effect of osteoarthritis (OA), rheumatoid arthritis (RA) and septic arthritis is the progressive loss of articular cartilage and thereby normal joint function. No marketed pharmaceutical agent is able to prevent or slow this cartilage loss, although nonsteroidal antiinflammatory drugs (NSAIDs) have been given to control pain and swelling. The end result of these diseases is total loss of joint function which is only treatable by joint replacement surgery. MMP inhibitors are expected to halt or reverse the progression of cartilage loss and obviate or delay surgical intervention.

Proteases are critical elements at several stages in the progression of metastatic cancer. In this process, the proteolytic degradation of structural protein in the basal membrane allows for expansion of a tumor in the primary site, evasion from this site as well as homing and invasion in distant, secondary sites. Also, tumor induced angiogenesis is required for tumor growth and is dependent on proteolytic tissue remodeling. Transfection experiments with various types of proteases have shown that the matrix metalloproteases play a dominant role in these processes in particular gelatinases A and B (MMP-2 and MMP-9, respectively). For an overview of this field see Mullins, et al., Biochim. Biophys. Acta 695, 177 (1983); Ray, et al., Eur. Respir. J. 7, 2062 (1994); Birkedal-Hansen, et al., Crit. Rev. Oral Biol. Med. 4, 197 (1993).

Furthermore, it was demonstrated that inhibition of degradation of extracellular matrix by the native matrix metalloprotease inhibitor TIMP-2 (a protein) arrests cancer growth (DeClerck, et al., Cancer Res. 52, 701 (1992)) and that TIMP-2 inhibits tumor-induced angiogenesis in experimental systems (Moses, et al. Science 248, 1408 (1990)). For a review, see DeClerck, et al., Ann. N. Y. Acad. Sci. 732, 222 (1994). It was further demonstrated that the synthetic matrix metalloprotease inhibitor batimastat when given intraperitoneally inhibits human colon tumor growth and spread in an orthotopic model in nude mice (Wang, et al. Cancer Res. 54, 4726 (1994)) and prolongs the survival of mice bearing human ovarian carcinoma xenografts (Davies, et. al., Cancer Res. 53, 2087 (1993)). The use of this and related compounds has been described in Brown, et al., WO-9321942 A2 (931111).

There are several patents and patent applications claiming the use of metalloproteinase inhibitors for the retardation of metastatic cancer, promoting tumor regression, inhibiting cancer cell proliferation, slowing or preventing cartilage loss associated with osteoarthritis or for treatment of other diseases as noted above (e.g. Levy, et al., WO-9519965 A1; Beckett, et al., WO-9519956 A1; Beckett, et al., WO-9519957 A1; Beckett, et al., WO-9519961 A1; Brown, et al., WO-9321942 A2; Crimmin, et al., WO-9421625 A1; Dickens, et al., U.S. Pat. No. 4,599,361; Hughes, et al., U.S. Pat. No. 5,190,937; Broadhurst, et al., EP 574758 A1; Broadhurst, et al., EP 276436; and Myers, et al., EP 520573 A1. The preferred compounds of these patents have peptide backbones with a zinc complexing group (hydroxamic acid, thiol, carboxylic acid or phosphinic acid) at one end and a variety of sidechains, both those found in the natural amino acids as well as those with more novel functional groups. Such small peptides are often poorly absorbed, exhibiting low oral bioavailability. They are also subject to rapid proteolytic metabolism, thus having short half lives. As an example, batimastat, the compound described in Brown, et al., WO-9321942 A2, can only be given intraperitoneally.

Others have disclosed a series of biphenyl-containing carboxylic acids, illustrated by the compound shown below, which inhibit neural endopeptidase (NEP 24.11), a membrane-bound zinc metalloprotease (Stanton, et al., Bioorg. Med. Chem. Lett. 4, 539, 1994; Lombaert, et al., Bioorg. Med. Chem. Lett. 4, 2715 (1994); Lombaert, et al., Bioorg. Med. Chem. Lett. 5, 145 (1995); Lombaert, et al., Bioorg. Med. Chem. Lett. 5, 151 (1995)).

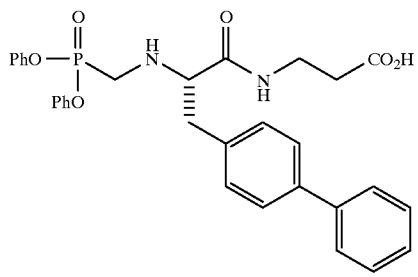

It has been reported that N-carboxyalkyl derivatives containing a biphenylethylglycine, illustrated by the compound shown below, are inhibitors of stromelysin-1 (MMP-3), 72 kDA gelatinase (MMP-2) and collagenase (Durette, et al., WO-9529689).

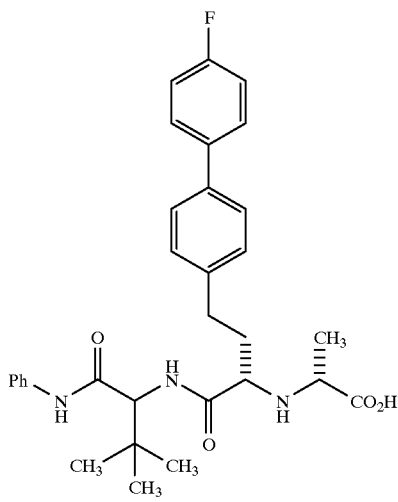

It would be desirable to have effective MMP inhibitors which possess improved bioavailability and biological stability relative to the peptide-based compounds of the prior art, and which can be optimized for use against particular target MMPs. Such compounds are the subject of the present application.

The development of efficacious MMP inhibitors would afford new therapies for diseases mediated by the presence of, or an excess of MMP activity, including osteoarthritis, rheumatoid arthritis, septic arthritis, tumor metastasis, periodontal diseases, corneal ulcerations, and proteinuria. Several inhibitors of MMPs have been described in the literature, including thiols (Beszant, et al., J. Med. Chem. 36, 4030 (1993)), hydroxamic acids (Wahl, et al. Bioorg. Med. Chem. Lett. 5, 349 (1995); Conway, et al. J. Exp. Med. 182, 449 (1995); Porter, et al., Bioorg. Med. Chem. Lett. 4, 2741 (1994); Tomczuk, et al., Bioorg. Med. Chem. Lett. 5, 343 (1995); Castelhano, et al., Bioorg. Med. Chem. Lett. 5, 1415 (1995)), phosphorous-based acids (Bird, et al. J. Med. Chem. 37, 158 (1994); Morphy, et al., Bioorg. Med. Chem. Lett. 4, 2747 (1994); Kortylewicz, et al., J. Med. Chem. 33, 263 (1990)), and carboxylic acids (Chapman, et al. J. Med. Chem. 36, 4293 (1993); Brown, et al. J. Med. Chem. 37, 674 (1994); Morphy, et al., Bioorg. Med. Chem. Lett. 4, 2747 (1994); Stack, et al., Arch. Biochem. Biophys. 287, 240 (1991); Ye, et al., J. Med. Chem. 37, 206 (1994); Grobelny, et al., Biochemistry 24, 6145 (1985); Mookhtiar, et al., Biochemistry 27, 4299 (1988)). However, these inhibitors generally contain peptidic backbones, and thus usually exhibit low oral bioactivity due to poor absorption and short half lives due to rapid proteolysis. Therefore, there remains a need for improved MMP inhibitors.

SUMMARY OF THE INVENTION

This invention provides compounds having matrix metalloprotease inhibitory activity. These compounds are useful for inhibiting matrix metalloproteases and, therefore, combating conditions to which MMPs contribute. Accordingly, the present invention also provides pharmaceutical compositions and methods for treating such conditions.

The compounds described relate to a method of treating a mammal comprising administering to the mammal a matrix metalloprotease inhibiting amount of a compound according to the invention sufficient to:

(a) alleviate the effects of osteoarthritis, rheumatoid arthritis, septic arthritis, periodontal disease, corneal ulceration, proteinuria, aneurysmal aortic disease, dystrophobic epidermolysis, bullosa, conditions leading to inflammatory responses, osteopenias mediated by MMP activity, tempero mandibular joint disease, demyelating diseases of the nervous system;

(b) retard tumor metastasis or degenerative cartilage loss following traumatic joint injury;

(c) reduce coronary thrombosis from athrosclerotic plaque rupture; or (d) effect birth control.

The compounds of the present invention are also useful scientific research tools for studying functions and mechanisms of action of matrix metalloproteases in both in vivo and in vitro systems. Because of their MMP-inhibiting activity, the present compounds can be used to modulate MMP action, thereby allowing the researcher to observe the effects of reduced MMP activity in the experimental biological system under study.

This invention relates to compounds having matrix metalloprotease inhibitory activity and the generalized formula

A-D-E-G  (L)

A represents alkyl; allyl-, benzyloxy-, or 3-propynyl alkyl groups as well as the structure:

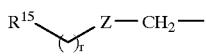

where $Z=(CH_2)_e$—$C_6H_4$—$(CH_2)_f$ or $(CH_2)_g$, e=0–8, f=0–5, g=0–14 and where r is 0–6.

$R^{15}$ may be —H, —Cl, —OMe or

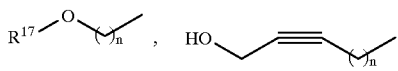

wherein n is 0–4, $R^{17}$ is —$C_2H_5$, -allyl, or -benzyl.

In the generalized formula (L), D represents

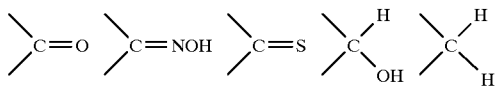

In the generalized formula (L), E represents a chain of n' carbon atoms bearing m substituents $R^6$ in which the $R^6$ groups are independent substituents, or constitute spiro or nonspiro rings. Rings may be formed in two ways: a) two groups $R^6$ are joined, and taken together with the chain atom(s) to which the two $R^6$ group(s) are attached, and any intervening chain atoms, constitute a 3–7 membered ring, or b) one group $R^6$ is joined to the chain on which this one group $R^6$ resides, and taken together with the chain atom(s) to which the $R^6$ group is attached, and any intervening chain atoms, constitutes a 3–7 membered ring. The number n' of carbon atoms in the chain is 2 or 3, and the number m of $R^6$ substituents is an integer of 1–3. The number of carbons in the totality of $R^6$ groups is at least two.

Each group $R^6$ is alkyl, alkenyl, alkynyl, aryl, heteroaryl, non-aromatic cyclic, and combinations thereof optionally substituted with one or more hetero-atoms as described more fully below.

In the generalized formula (L), G represents —$CO_2H$, —$PO_3H_2$, -M,

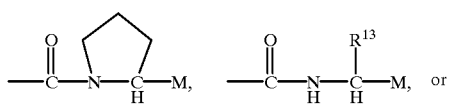

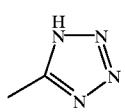

in which M represents —$CO_2H$, —$CON(R^{11})_2$, or —$CO_2R^{12}$, where $R^{11}$ is H or alkyl of 1–4 carbons, $R^{12}$ is alkyl of 1–4 carbons, and $R^{13}$ represents any of the side chains of the 19 noncyclic naturally occurring amino acids.

Certain embodiments include compounds having matrix metalloproteinase inhibitory activity and the following generalized formula:

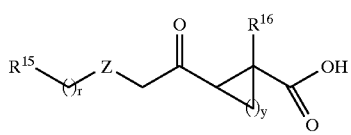

where Z=$(CH_2)_e$—$C_6H_4$—$(CH_2)_f$ or $(CH_2)_g$, e=0–8, f=0–5, g=0–14 and where y is 0, 2, or 3.

$R^{15}$ may be H, Cl, MeO or

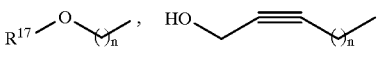

wherein n is 0–4, $R^{17}$ is $C_2H_5$, allyl, or benzyl, and $R^{16}$ is one of

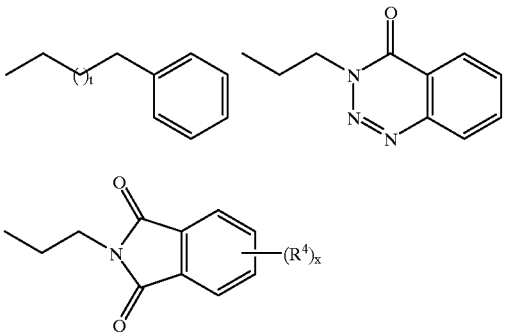

where t is 0–2, x is 0–4 and $R^4$ is one of the following: halide, alkyl of 1–6 carbons, OR, $NR_2$, $NO_2$ (R=H or alkyl of 1–6 carbons).

The foregoing merely summarizes certain aspects of the present invention and is not intended, nor should it be construed, to limit the invention in any way. All of the patents and other publications recited in this specification are hereby incorporated by reference in their entirety.

DESCRIPTION OF THE PREFERRED EMBODIMENTS

More particularly, the compounds of the present invention are materials having matrix metalloprotease inhibitory activity and the generalized formula:

A-D-E-G    (L)

in which A represents alkyl of 9–14 carbons or alkyloxy of 9–18 carbons, or allyloxy-, benzyloxy-, or propynyl-alkyl of 9–18 carbons. A is also represented by the structure:

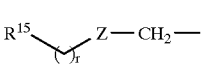

where Z=$(CH_2)_e$—$C_6H_4$—$(CH_2)_f$ or $(CH_2)_g$, e=0–8, f=0–5, g=0–14 and where r is 0–6.

$R^{15}$ may be —H, —Cl, —OMe or

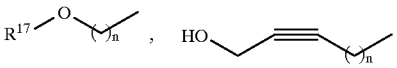

wherein n is 0–4, $R^{17}$ is $C_2H_5$, allyl, or benzyl.

In the generalized formula (L), D represents the moieties

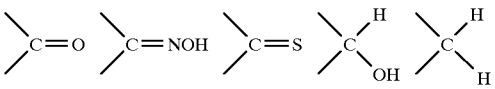

Throughout this application, in the displayed chemical structures, an open bond indicates the point at which the structure joins to another group. For example,

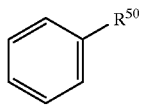

where $R^{50}$ is

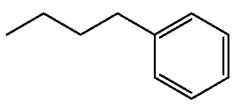

is the structure

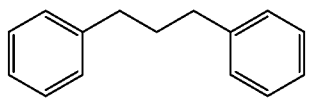

In the generalized formula (L), E represents a chain of n carbon atoms bearing m substituents $R^6$, referred to as $R^6$ groups or $R^6$ units. The $R^6$ groups are independent substituents, or constitute spiro or nonspiro rings. Rings may be formed in two ways: a) two groups $R^6$ are joined, and taken together with the chain atom(s) to which the two $R^6$ group(s) are attached, and any intervening chain atoms, constitute a 3–7 membered ring, or b) one group $R^6$ is joined to the chain on which this one group $R^6$ resides, and taken together with the chain atom(s) to which the $R^6$ group is attached, and any intervening chain atoms, constitutes a 3–7 membered ring. The number n of carbon atoms in the chain is 2 or 3, and the number m of $R^6$ substituents is an integer of 1–3. The number of carbons in the totality of $R^6$ groups is at least two.

Each group $R^6$ is independently selected from the group consisting of the substituents listed below as items 1)–14):

1) alkyl of 1–10 carbons;
2) aryl of 6–10 carbons;
3) heteroaryl comprising 4–9 carbons and at least one N, O, or S heteroatom;
4) arylalkyl in which the aryl portion contains 6–10 carbons and the alkyl portion contains 1–8 carbons;
5) heteroaryl-alkyl in which the heteroaryl portion comprises 4–9 carbons and at least one N, O, or S heteroatom, and the alkyl portion contains 1–8 carbons;
6) alkenyl of 2–10 carbons;
7) aryl-alkenyl in which the aryl portion contains 6–10 carbons and the alkenyl portion contains 2–5 carbons;
8) heteroaryl-alkenyl in which the heteroaryl portion comprises 4–9 carbons and at least one N, O, or S heteroatom and the alkenyl portion contains 2–5 carbons;
9) alkynyl of 2–10 carbons;
10) aryl-alkynyl in which the aryl portion contains 6–10 carbons and the alkynyl portion contains 2–5 carbons;
11) heteroaryl-alkynyl in which the heteroaryl portion comprises 4–9 carbons and at least one N, O, or S heteroatom and the alkynyl portion contains 2–5 carbons;
12) —$(CH_2)_tR^7$ in which t is 0 or an integer of 1–5 and $R^7$ is selected from the group consisting of:

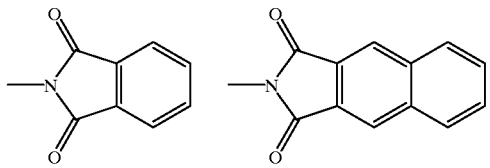

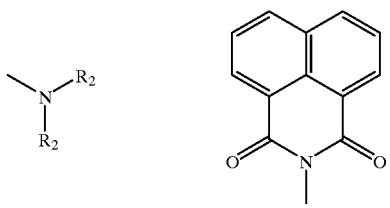

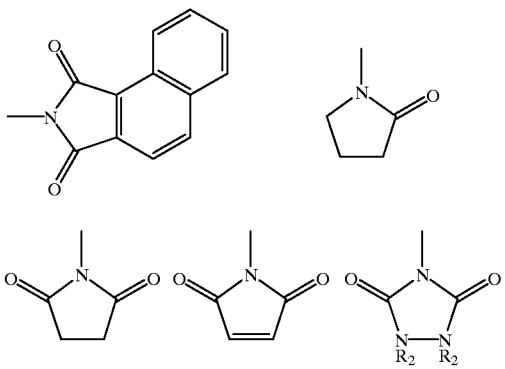

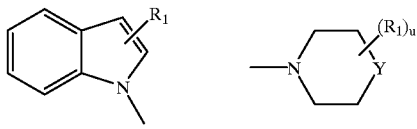

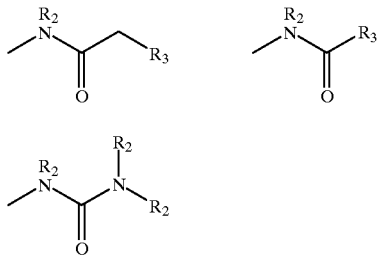

as well as corresponding heteroaryl moieties in which the aryl portion of an aryl-containing $R^7$ group comprises 4–9 carbons and at least one N, O, or S heteroatom. In such $R^7$ groups, Y represents O or S; and u is 0, 1, or 2 provided that when $R^7$ is

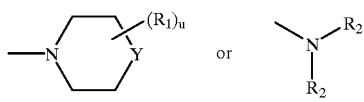

and the A unit is phenyl, the B unit is phenylene, m is 1, n is 2, and t is 0, and x is 1 or 2.

$R^1$ represents H or alkyl of 1–3 carbons. $R^2$ represents H; alkyl of 1–6 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; or heteroaryl-alkyl in which the heteroaryl portion comprises 4–9 carbons and at least one N, O, or S heteroatom and the alkyl portion contains 1–4 carbons.

$R^3$ represents alkyl of 1–4 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; or heteroaryl-alkyl in which the heteroaryl portion comprises 4–9 carbons and at least one N, O, or S heteroatom and the alkyl portion contains 1–4 carbons.

13) —$(CH_2)_v P'R^8$ in which v is an interger of 1 to 4, P' represents —S—, —S(O)—, —SO$_2$—, or —O— and $R^8$ is selected from the group consisting of alkyl of 1 to 12 carbons; aryl of 6 to 10 carbons; heteroaryl comprising 4 to 9 carbons and at least one N, O, or S heteroatom; arylalkyl in which the aryl portion contains 6 to 12 carbons and the alkyl portion contains 1 to 4 carbons; heteroarylalkyl in which the aryl portion contains 6 to 12 carbons and at least one N, O, or S heteroatom and the alkyl portion contains 1 to 4 carbons; —C(O)$R^9$ in which the $R^9$ represents alkyl of 2 to 6 carbons, aryl of 6 to 10 carbons, heteroaryl comprising 4 to 9 carbons and at least one N, O, or S heteroatom; and arylalkyl in which the aryl portion contains 6 to 10 carbons or is a heteroaryl comprising 4 to 9 carbons and at least one N, O, or S heteroatom, and the alkyl portion contains 1 to 4 carbons, with the provisos that when $R^8$ is —C(O)$R^9$, Z is —S— or —O—; when Z is —O—, $R^8$ may also be —$(C_9H_{2q}O)_rR^5$, and when the A unit is phenyl, the B unit is phenylene, m is 1, n is 2, and v is 0, then x is 1 or 2.

14) —$(CH_2)_w SiR^{10}_3$ in which w is an integer of 1 to 3, and $R^{10}$ represents alkyl of 1 to 2 carbons.

In addition, aryl or heteroaryl portions of any of the $R^6$ groups optionally may bear up to two substituents selected from the group consisting of —$(CH_2)_{y'}C(R^{11})(R^{12})OH$, —$(CH_2)_{y'}OR^{11}$, —$(CH_2)_{y'}SR^{11}$, —$(CH_2)_{y'}S(O)R^{11}$, —$(CH_2)_{y'}S(O)_2R$, —$(CH_2)_{y'}SO_2N(R^{11})_2$, —$(CH_2)_{y'}N(R^{11})_2$, —$(CH_2)_{y'}N(R^{11})COR$, —$OC(R^{11})_2O$— in which both oxygen atoms are connected to the aryl ring, —$(CH_2)_{y'}COR^{11}$, —$(CH_2)_{y'}CON(R^{11})_2$, —$(CH_2)_{y'}CO_2R^{11}$, —$(CH_2)_{y'}OCOR^{11}$-halogen —CHO, —CF$_3$, —NO$_2$, —CN, and —$R^{12}$, in which y' is 0–4; $R^{11}$ represents H or alkyl of 1–4 carbons; and $R^{12}$ represents alkyl of 1–4 carbons.

In the generalized formula (L), G represents —CO$_2$H, —PO$_3$H$_2$, -M,

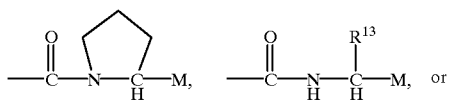 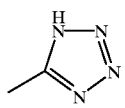

in which M represents —CO$_2$H, —CON(R$^{11}$)$_2$, or —CO$_2$R$^{12}$, and R$^{13}$ represents any of the side chains of the 19 noncyclic naturally occurring amino acids.

Pharmaceutically acceptable salts of the compounds falling within the generalized formula (L) are also within the invention.

It is to be understood that as used herein, the term "alkyl" means straight, branched, cyclic, and polycyclic materials.

The term "haloalkyl" means partially or fully halogenated alkyl groups such as —(CH$_2$)$_2$Cl, —CF$_3$ and —C$_6$F$_{13}$, for example.

In one embodiment, the invention relates to compounds of generalized formula (L), wherein n is 2 and m is 1 in the E unit. These compounds thus possess two carbon atoms between the D unit and the G unit, and carry one substituent on this two-carbon chain.

In another of its embodiments, the invention relates to compounds of generalized formula (L) in which the number of substituents m on the E unit is 2 or 3; and when m is 2, both groups $R^6$ are independent substituents, or together constitute a spiro ring, or one group $R^6$ is an independent substituent and the other constitutes a spiro ring; and when m is 3, two groups $R^6$ are independent substituents and one group $R^6$ constitutes a ring, or two groups $R^6$ constitute a ring and one group R6 is an independent substituent, or three groups $R^6$ are independent substituents. This subset therefore contains compounds in which the E unit is di- or tri-substituted, and in the disubstituted case any rings formed by one or both $R^6$ groups are spiro rings, and in the trisubstituted case, the $R^6$ groups may form either spiro or nonspiro rings.

In another of its embodiments, the invention relates to compounds of generalized formula (L) in which the number of substituents m on the E unit is 1 or 2; and when m is 1, the group $R^6$ constitutes a nonspiro ring; and when m is 2, both groups $R^6$ together constitute a nonspiro ring or one group $R^6$ is an independent substituent and the other constitutes a nonspiro ring. This subset therefore contains compounds in which the E unit carries one or two substituents $R^6$, and at least one of these substituents is involved in a nonspiro ring.

More particularly, representative compounds of generalized formula (L) in which one or more of the substituent groups $R^6$ are involved in formation of nonspiro rings have E units of the following structures:

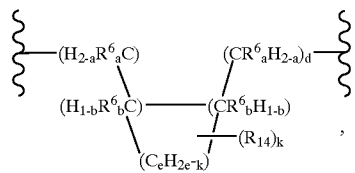

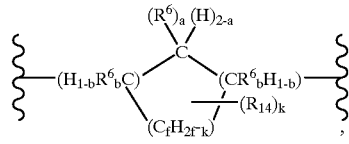

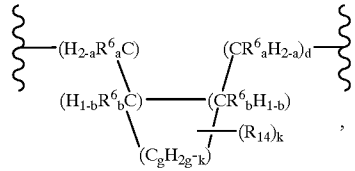

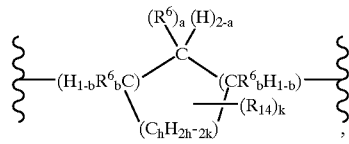

-continued

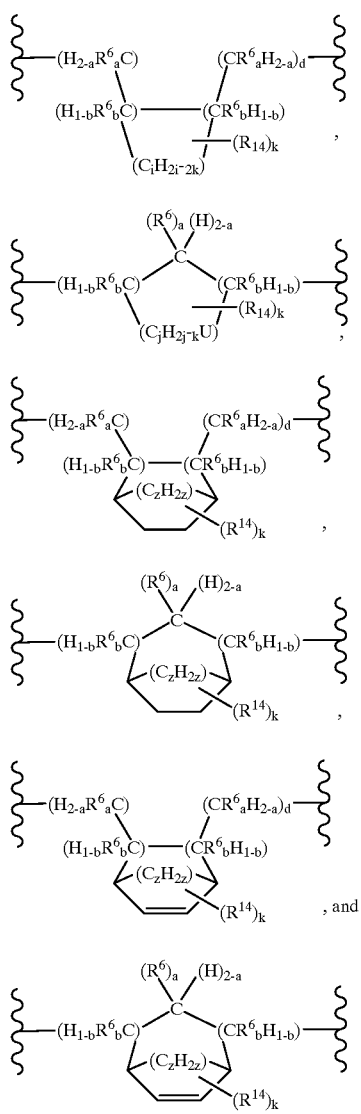

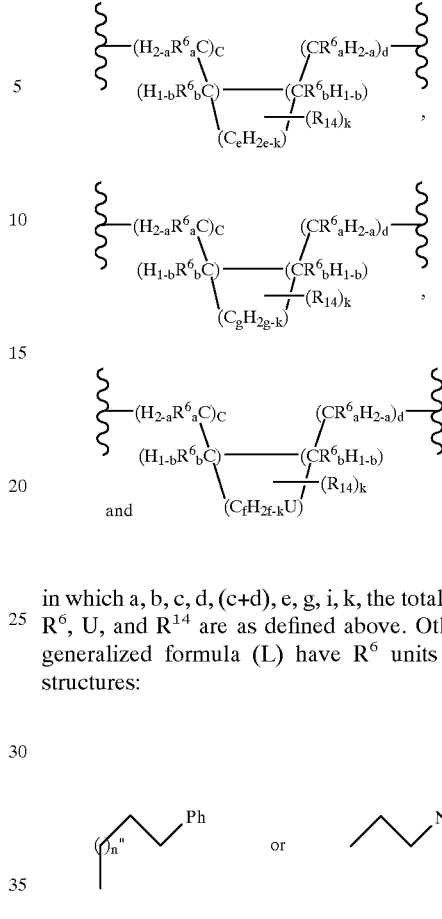

in which a is 0, 1, or 2; b is 0 or 1; c is 0 or 1; d is 0 or 1; c+d is 0 or 1; e is 1–5; f is 1–4; g is 3–5; h is 2–4; i is 0–4; j is 0–3; k is 0–2; the total number of groups $R^6$ is 0, 1, or 2; U represents O, S, or $NR^1$; and z is 1 or 2; Each group $R^{14}$ is independently selected from the group consisting of alkyl of 1–9 carbons; arylalkyl in which the alkyl portion contains 1–7 carbons and the aryl portion contains 6–10 carbons; alkenyl of 2–9 carbons; aryl-substituted alkenyl in which the alkenyl portion contains 2–4 carbons and the aryl portion contains 6 - 10 carbons; alkynyl of 2–9 carbons; aryl-substituted alkynyl in which the alkynyl portion contains 2–4 carbons and the aryl portion contains 6–10 carbons; aryl of 6–10 carbons; —$COR^2$; —$CO_2R^3$; —$CON(R^2)_2$; —$(CH_2)_tR^7$ in which t is 0 or an integer of 1–4; and —$(CH_2)_vZ'R^8$ in which v is 0 or an integer of 1 to 3, and Z' represents —S— or —O—. $R^1$, $R^2$, $R^3$, $R^6$, $R^7$, and $R^8$ have been defined above.

Preferred compounds of generalized formula (L) in which one or more of the substituent groups $R^6$ are involved in formation of nonspiro rings have E units of the following structures:

in which a, b, c, d, (c+d), e, g, i, k, the total number of groups $R^6$, U, and $R^{14}$ are as defined above. Other compounds of generalized formula (L) have $R^6$ units of the following structures:

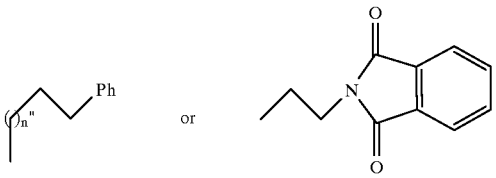

where n" is 0–1.

Most preferred compounds of the general formula (L) include those of the following general formula

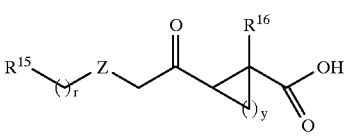

wherein y is 0 (i.e., there is no ring structure), 2 (cyclobutyl), or 3 (cyclopentyl), r is 0–6, Z is $(CH_2)_7$ or $(CH_2)_e$—$C_6H_4$—$(CH_2)_f$, wherein e is 0–1 and f is 0–5, and $R^{15}$ is —H, —Cl, —OMe or

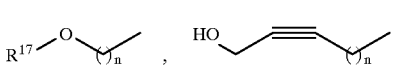

wherein n is 0–4, $R^{17}$ is —$C_2H_5$, -allyl, -benzyl, and $R^{16}$ is

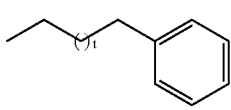

-continued

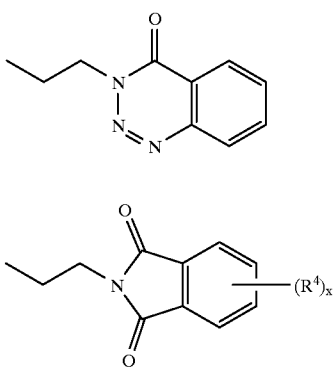

where x is 0–4, t is 0–2, and $R^4$ is one of the following: halide, alkyl of 1–6 carbons, OR, $NR_2$, $NO_2$ (R=H or alkyl of 1–6 carbons).

Those skilled in the art will appreciate that many of the compounds of the invention exist in enantiomeric or diastereomeric forms, and that it is understood by the art that such stereoisomers generally exhibit different activities in biological systems. This invention encompasses all possible stereoisomers which possess inhibitory activity against an MMP, regardless of their stereoisomeric designations, as well as mixtures of stereoisomers in which at least one member possesses inhibitory activity.

The most prefered compounds of the present invention are as indicated and named in the list below:
I) 1,3-dihydro-1,3-dioxo-α-(2-oxododecyl)-2H-isoindole-2-butanoic acid,
II) 1,3-dihydro-1,3-dioxo-α-(2-oxoundecyl)-2H-isoindole-2-butanoic acid,
III) 1,3-dihydro-1,3-dioxo-α-(2-oxotidecyl)-2H-isoindole-2-butanoic acid,
IV) 1,3-dihydro-1,3-dioxo-α-(2-oxotetradecyl)-2H-isoindole-2-butanoic acid,
V) 1,3-dihydro-1,3-dioxo-α-(2-oxopentadecyl)-2H-isoindole-2-butanoic acid,
VI) 1,3-dihydro-1,3-dioxo-α-(2-oxohexadecyl)-2H-isoindole-2-butanoic acid,
VII) γ-oxo-α-(2-phenylethyl)-benzeneheptanoic acid,
VIII) γ-oxo-α-(2-phenylethyl)-benzenehexanoic acid, and
IX) γ-oxo-α-(2-phenylethyl)-benzenepentanoic acid The compounds of the invention may be prepared by use of known chemical reactions and procedures. Nevertheless, the following general preparative methods are presented to aide the reader in synthesizing the inhibitors. More detailed procedures for particular examples are presented below in the experimental section.

In the general methods the following generic descriptions apply. The group designated P represents a protecting group. It may be appreciated by one skilled in the act that a variety of different protecting groups may be used to protect a potentially reactive functional group (e.g. carboxylic acid, alcohol) and that the particular choice will depend upon the reaction conditions required to prepare a given target compound. A description of such protecting groups may be found in: Green and Wuts, Protective Groups in Organic Synthesis, 2nd Ed., John Wiley and Sons, New York, 1991.

The group designated X represents a leaving group, It is well known to those skilled in the an that several different functional groups such as halides, mesylates, tosylates and triflates may serve as a leaving groups. It is also known that the choice of a particular leaving group typically depends on such factors as the reactivity of the nucleophile, stability of the compound and ease of synthesis.

General Method A-The compounds of the invention where E does not contain a ring are conveniently prepared using an (α-halomethyl ketone and a substituted malonate derivative. The α-halomethyl ketone intermediate CIII (X=Cl, Br) can be conveniently prepared from a carboxylic acid or a methyl ketone. From carboxylic acid CI, treatment with oxalyl chloride and a catalytic amount of DMF in a solvent like trimethylsilylchloride provides the corresponding acid chloride. Subsequent treatment with excess diazomethane followed by anhydrous HCl or HBr provides intermediate CIII. Alternatively, intermediate CIII can be prepared from methyl ketone CII via the corresponding silyl enol ether by treatment with N-bromosuccinimide (NBS). The silylenol ether is conveniently prepared from the methyl ketone by treatment with triniethylsilylchlotide (TMSCI) and a base like lithium hexamethyldisilazide (LHMDS). General procedures for the preparation of α-halomethyl ketones are well-known to those skilled in the art. For additional references see Corey, et al., Tetrahedron Lett. 25, 495 (1984) and Reuss, et al., J. Org. Chem. 39, 1785 (1974).

Methods for the preparation of substituted malonate derivatives (CV) are also well-established in the literature. Typically, an unsubstituted malonate derivative is treated with a base like NaH or KOt-Bu in a polar aprotic solvent, and then alkylated with a substituted halide. Similarly, alkylation of mono alkylated intermediate CV with α-halomethyl ketone CIII provides dialkylated intermediate, CVI. It should be appreciated by those skilled in the art that sidechain Y may be the sidechain desired in the final target or a simple handle to further elaborate that portion of the molecule at a latter stage of the synthesis. If sidechain Y is the desired sidechain, then intermediate CVI can simply be deprotected and decarboxylated using well-known procedures to give target compound CVIII. The conditions used to deprotect intermediate CVI will depend on the type of protecting group used. Some convenient protecting groups used to synthesize the compounds of the invention include methyl, allyl, benzyl and tert-butyl. Methods to incorporate and remove these groups are well-known to those skilled in the art (see above reference). The choice of protecting group used in the synthesis will depend on such factors as functional group compatibility, ease of synthesis and availability of starting materials.

If the target compound CXI contains a moiety Q which is sensitive to the reaction conditions used in the alkylation steps then an intermediate sidechain Y can be used. In this case, a protected ethanol group such as $CH_2CH_2OTBS$ can be conveniently incorporated as this handle. Intermediate CV with Y=—$CH_2CH_2OTBS$ can be prepared by using $TBSOCH_2CH_2Br$ as Y-X in the first alkylation step. $TBSOCH_2CH_2Br$ can be prepared from $HOH_2CH_2Br$ by methods well-known to those skilled in the art. The protecting group can be removed to provide the corresponding alcohol which may be converted to phenyl ethers or a variety of heteroatom substituted derivatives used to generate sidechain Q via the Mitsunobu reaction. The Mitsunobu reaction is well known to those skilled in the art; see Mitsunobu, Synthesis 1 (1981), and Hughes, Organic Reactions 42, 335 (1992). Alternatively, the alcohol intermediate is converted to a leaving group such as tosylate or bromide and displaced by an appropriate nucleophile. Several examples of this type of reaction can be found in Norman, et al., J. Med. Chem. 37, 2552 (1994). After the desired sidechain Q is incorporated to form CX, the malonate moiety can be deprotected and decarboxylated to provide the target compound CXI. In some cases the ketone moiety of intermediate CIII may need to be protected to avoid undesired side reactions. If required, protection as an acetal using the protocols like those described in Hwu, et al., J. Org, Chem. 50, 3946 (1985), is generally preferred.

the identity of side chain function J. Reaction of MV with Wittig reagents followed by hydrogenation yields products in which J is alkyl, aryl or arylalkyl. Selective reduction of aldehyde MV with a reducing agent such as lithium tris[(3-ethyl-3-pentyl)oxy]aluminum hydride (LTEPA) yields alcohol MVI. The alcohol may be converted to phenyl ethers or a variety of heteroatom substituted derivatives used to generate sidechain $R^{16}$ via the Mitsunobu reaction. The Mitsunobu reaction is well known to those skilled in the art; see Mitsunobu, Synthesis 1 (1981), and Hughes, Organic Reactions, 42, 335 (1992). Alternatively alcohol MVI is

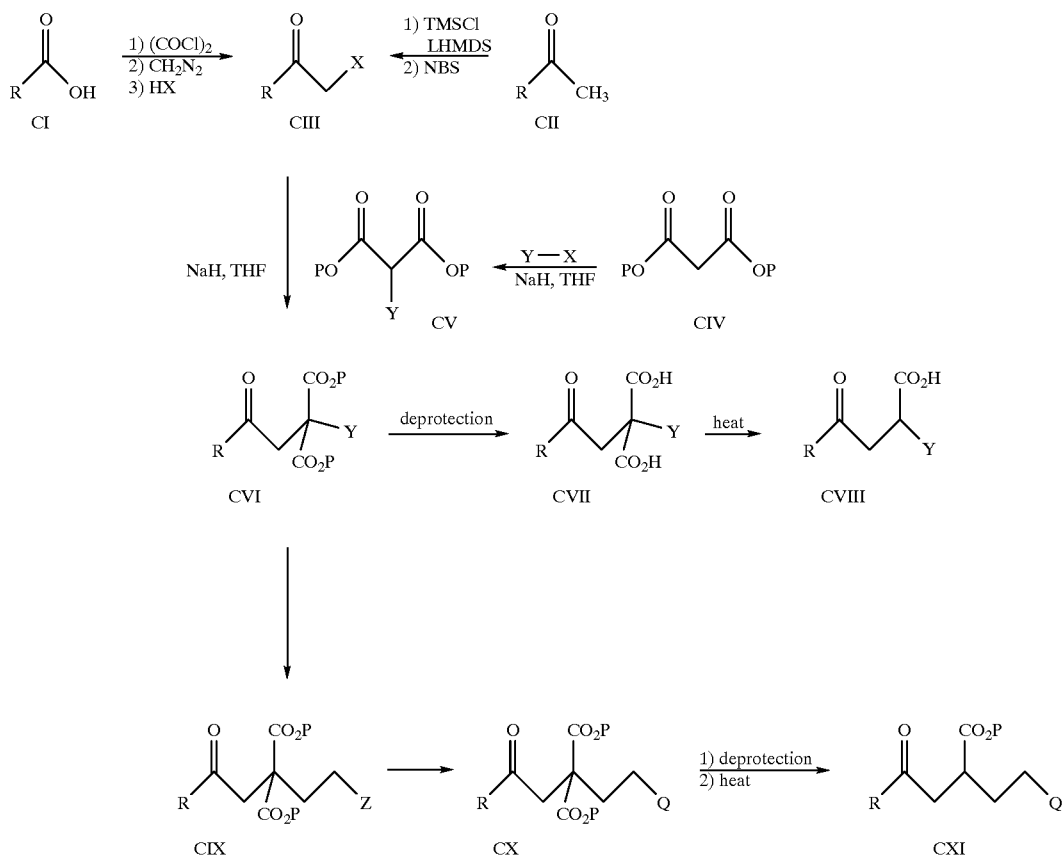

General Method B-The compounds of this invention in which two $R^6$ groups are joined to form a substituted 5-member ring E are most conveniently prepared by method B. In this method acid MI (R=H) is prepared using the protocols described in Beeley, et al., Tetrahedron 37 Suppl., 411 (1981). The acid is protected as an ester [e.g., R=benzyl (Bn) or 2-(trimethylsilyl)ethyl (TMSE)] by use of coupling agents such as 1-(3-dimnethylaminopropyl-3-ethylcarbodiimide) hydrochloride and procedures well known to those skilled in the art. The Grignard reagent MII [prepared from the corresponding bromide by treatment with magnesium] is reacted with MI (R=Bn, TMSE) to yield alcohol MMIII. Alcohol MIII is eliminated via base treatment of its mesylate using conditions well known to those skilled in the art to yield olefin MIV. Ozonolysis of MIV (workup with methysulfide) yields aldehyde MV. Alternatively, treatment with $OsO_4$ followed by $H_5IO_6$ converts MIV to MV.

Conversion of key intermediate MV to the targeted patent compounds is accomplished in several ways depending on converted to a leaving group such as tosylate MVII or bromide by conditions well known to those skilled in the art and then the leaving group is displaced by the appropriate nucleophile. Several examples of this type of reaction can be found in Norman, et al., Med. Chem. 37, 2552 (1994). Direct acylation of the alcohol MVI yields compounds in which J=OAcyl and reaction of the alcohol with various alkyl halides in the presence of base yields alkyl ethers. In each case a final step is removal of acid blocking group R to yield acids (R=H) by using conditions which depend on the stability of R and J, but in all cases well known to those skilled in the art. Removal of the benzyl group, for example, may be accomplished by base hydrolysis or hydrogenolysis, whereas deprotection of the 2-(trimethylsilyl)ethyl ester is typically carried out by simple treatment with tetrabutylammonium fluoride.

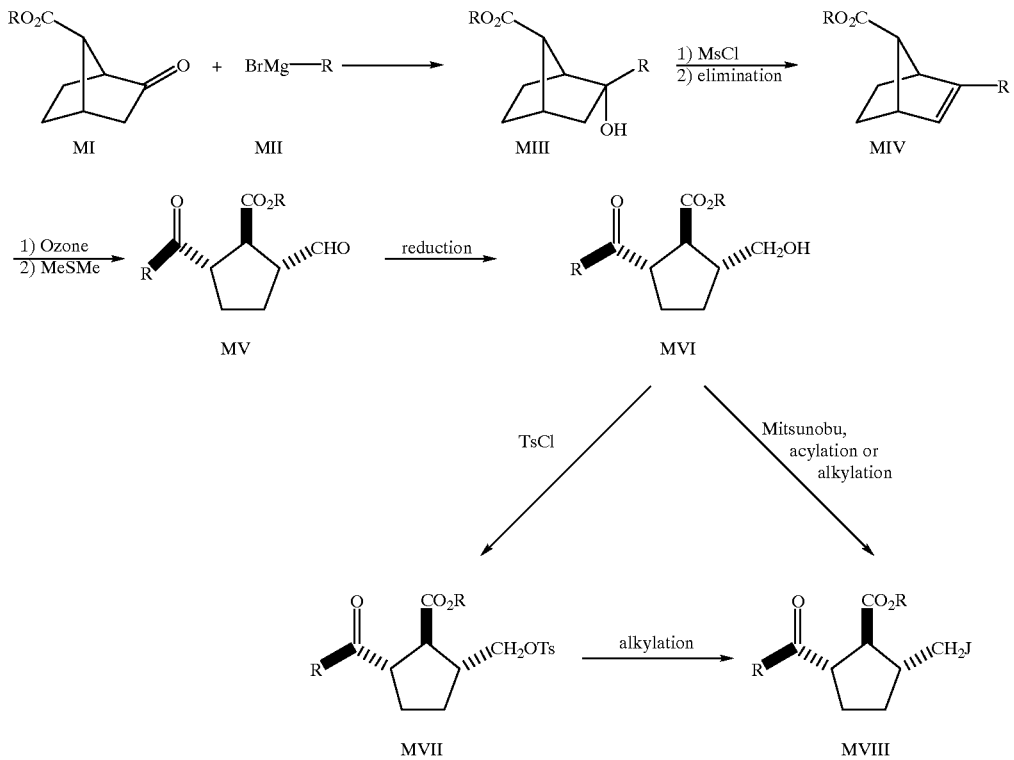

Suitable pharmaceutically acceptable salts of the compounds of the present invention include addition salts formed with organic or inorganic bases. The salt forming ion derived from such bases can be metal ions, e.g., aluminum, alkali metal ions, such as sodium or potassium, alkaline earth metal ions such as calcium or magnesium, or an amine salt ion, of which a number are known for this purpose. Examples include ammonium salts, arylalkylamines such as dibenzylamine and N,N-dibenzylethylenediamine, lower alkylamines such as methylamine, t-butylamine, procaine, lower alkylpiperidines such as N-ethylpiperidine, cycloalkylamines such as cyclohexylamine or dicyclohexylamine, 1-adamantylamine, benzathine, or salts derived from amino acids like arginine, lysine or the like. The physiologically acceptable salts such as the sodium or potassium salts and the amino acid salts can be used medicinally as described below and are preferred.

These and other salts which are not necessarily physiologically acceptable are useful in isolating or purifying a product acceptable for the purposes described below. For example, the use of commercially available enantiomerically pure amines such as (+)-cinchonine in suitable solvents can yield salt crystals of a single enatiomer of the invention compounds, leaving the opposite enantiomer in solution in a process often referred to as "classical resolution." As one enantiomer of a given invention compound is usually substantially greater in physiological effect than its antipode, this active isomer can thus be found purified in either the crystals or the liquid phase. The salts are produced by reacting the acid form of the invention compound with an equivalent of the base supplying the desired basic ion in a medium in which the salt precipitates or in aqueous medium and then lyophilizing. The free acid form can be obtained from the salt by conventional neutralization techniques, e.g., with potassium bisulfate, hydrochloric acid, etc.

The compounds of the present invention have been found to inhibit the matrix metalloproteases MMP-3, MMP-9 and MMP-2, and to a lesser extent MMP-1, and are therefore useful for treating or preventing the conditions referred to in the background section. As other MMPs not listed above share a high degree of homology with those listed above, especially in the catalytic site, it is deemed that compounds of the invention should also inhibit such other MMPs to varying degrees. Varying the substituents on the biaryl portions of the molecules, as well as those of the propanoic or butanoic acid chains of the claimed compounds, has been demonstrated to affect the relative inhibition of the listed MMPs. Thus compounds of this general class can be "tuned" by selecting specific substituents such that inhibition of specific MMP(s) associated with specific pathological conditions can be enhanced while leaving non-involved MMPs less affected.

The method of treating matrix metalloprotease-mediated conditions may be practiced in mammals, including humans, which exhibit such conditions.

The inhibitors of the present invention are contemplated for use in veterinary and human applications. For such purposes, they will be employed in pharmaceutical compositions containing active ingredient(s) plus one or more pharmaceutically acceptable carriers, diluents, fillers, binders, and other excipients, depending on the administration mode and dosage form contemplated.

Administration of the inhibitors may be by any suitable mode known to those skilled in the art. Examples of suitable parenteral administration include intravenous, intraarticular, subcutaneous and intramuscular routes. Intravenous administration can be used to obtain acute regulation of peak plasma concentrations of the drug. Improved half-life and targeting of the drug to the joint cavities may be aided by entrapment of the drug in liposomes. It may be possible to improve the selectivity of liposomal targeting to the joint cavities by incorporation of ligands into the outside of the liposomes that bind to synovial-specific macromolecules.

Alternatively intramuscular, intraarticular or subcutaneous depot injection with or without encapsulation of the drug into degradable microspheres e.g., comprising poly(DL-lactide-co-glycolide) may be used to obtain prolonged sustained drug release. For improved convenience of the dosage form it may be possible to use an i.p. implanted reservoir and septum such as the Percuseal system available from Pharmacia. Improved convenience and patient compliance may also be achieved by the use of either injector pens (e.g. the Novo Pin or Q-pen) or needle-free jet injectors (e.g. from Bioject, Mediject or Becton Dickinson). Prolonged zero-order or other precisely controlled release such as pulsatile release can also be achieved as needed using implantable pumps with delivery of the drug through a cannula into the synovial spaces. Examples include the subcutaneously implanted osmotic pumps available from ALZA, such as the ALZET osmotic pump.

Nasal delivery may be achieved by incorporation of the drug into bioadhesive particulate carriers (<200 μm) such as those comprising cellulose, polyacrylate or polycarbophil, in conjunction with suitable absorption enhancers such as phospholipids or acylcarnitines. Available systems include those developed by DanBiosys and Scios Nova.

A noteworthy attribute of the compounds of the present invention in contrast to those of various peptidic compounds referenced in the background section of this application is the demonstrated oral activity of the present compounds. Certain compounds have shown oral bioavailability in various animal models of up to 90–98%. Oral delivery may be achieved by incorporation of the drug into tablets, coated tablets, dragées, hard and soft gelatine capsules, solutions, emulsions or suspensions. Oral delivery may also be achieved by incorporation of the drug into enteric coated capsules designed to release the drug into the colon where digestive protease activity is low. Examples include the OROS-CT/Osmet™ and PULSINCAP™ systems from ALZA and Scherer Drug Delivery Systems respectively. Other systems use azo-crosslinked polymers that are degraded by colon specific bacterial azoreductases, or pH sensitive polyacrylate polymers that are activated by the rise in pH at the colon. The above systems may be used in conjunction with a wide range of available absorption enhancers.

Rectal delivery may be achieved by incorporation of the drug into suppositories.

The compounds of this invention can be manufactured into the above listed formulations by the addition of various therapeutically inert, inorganic or organic carriers well known to those skilled in the art. Examples of these include, but are not limited to, lactose, corn starch or derivatives thereof, talc, vegetable oils, waxes, fats, polyols such as polyethylene glycol, water, saccharose, alcohols, glycerin and the like. Various preservatives, emulsifiers, dispersants, flavorants, wetting agents, antioxidants, sweeteners, colorants, stabilizers, salts, buffers and the like are also added, as required to assist in the stabilization of the formulation or to assist in increasing bioavailability of the active ingredient(s) or to yield a formulation of acceptable flavor or odor in the case of oral dosing.

The amount of the pharmaceutical composition to be employed will depend on the recipient and the condition being treated. The requisite amount may be determined without undue experimentation by protocols known to those skilled in the art. Alternatively, the requisite amount may be calculated, based on a determination of the amount of target enzyme which must be inhibited in order to treat the condition.

The matrix metalloprotease inhibitors of the invention are useful not only for treatment of the physiological conditions discussed above, but are also useful in such activities as purification of metalloproteases and testing for matrix metalloprotease activity. Such activity testing can be both in vitro using natural or synthetic enzyme preparations or in vivo using, for example, animal models in which abnormal destructive enzyme levels are found spontaneously (use of genetically mutated or transgenic animals) or are induced by administration of exogenous agents or by surgery which disrupts joint stability.

The following examples are offered for illustrative purposes only and are not intended, nor should they be construed, to limit the invention in any way.

EXAMPLES

General Procedures:

All reactions were performed in flame-dried or oven-dried glassware under a positive pressure of argon and were stirred magnetically unless otherwise indicated. Sensitive liquids and solutions were transferred via syringe or cannula and were introduced into reaction vessels through rubber septa. Reaction product solutions were concentrated using a Buchi evaporator unless otherwise indicated.

Materials:

Commercial grade reagents and solvents were used without further purification except that diethyl ether and tetrahydrofuran were usually distilled under argon from benzophenone ketyl, and methylene chloride was distilled under argon from calcium hydride. Many of the specialty organic or organometallic starting materials and reagents were obtained from Aldrich, 1001 West Saint Paul Avenue, Milwaukee, Wis. 53233. Solvents are often obtained from EM Science as distributed by VWR Scientific.

Chromatography:

Analytical thin-layer chromatography (TLC) was performed on Whatman® pre-coated glass-backed silica gel 60 A F-254 250 μm plates. Visualization of spots was effected by one of the following techniques: (a) ultraviolet illumination, (b) exposure to iodine vapor, (c) immersion of the plate in a 10% solution of phosphomolybdic acid in ethanol followed by heating, and (d) immersion of the plate in a 3% solution of p-anisaldehyde in ethanol containing 0.5% concentrated sulfuric acid followed by heating.

Column chromatography was performed using 230–400 mesh EM Science® silica gel.

Analytical high performance liquid chromatography (HPLC) was performed at 1 mL min$^{-1}$ on a 4.6×250 mm Microsorb® column monitored at 288 nm, and semi-preparative HPLC was performed at 24 mL min$^{-1}$ on a 21.4×250 mm Microsorb® column monitored at 288 nm.

Instrumentation:

Melting points (mp) were determined with a Thomas-Hoover melting point apparatus and are uncorrected.

Proton ($^1$H) nuclear magnetic resonance (NMR) spectra were measured with a General Electric GN-OMEGA 300 (300 MHz) spectrometer, and carbon thirteen ($^{13}$C) NMR spectra were measured with a General Electric GN-OMEGA 300 (75 MHz) spectrometer. Most of the compounds synthesized in the experiments below were analyzed by nmr, and the spectra were consistent with the proposed structures in each case.

Mass spectral (MS) data were obtained on a Kratos Concept 1-H spectrometer by liquid-cesium secondary ion (LCIMS), an updated version of fast atom bombardment (FAB). Most of the compounds synthesized in the experiments below were analyzed by mass spectroscopy, and the spectra were consistent with the proposed structures in each case.

General Comments:

For multi-step procedures, sequential steps are noted by numbers.

Examples 1–6—Preparation of Compounds I–VI

Step 1 A solution of sodium hydride (4.35 g, 181 mmol) in freshly distilled THF (100 mL) was cooled to 0° C. and treated with commercially available diallyl malonate (35.0 g, 190 mmol) over 40 min via a dropping funnel. After stirring at room temperature for 30 min, N-(2-bromoethyl) phthalimide (43.9 g, 247 mmol) was added to the solution in one portion and the mixture was heated at reflux. After 48 h the solution was cooled to 0° C., quenched with 2N HCl and concentrated to about 20% of its original volume. The concentrate was diluted with ethyl acetate (300 mL) and washed successively with saturated aqueous solutions of $K_2CO_3$ and NaCl. The organic layer was dried over $MgSO_4$, filtered and concentrated under reduced pressure. Purification by flash column chromatography (gradient elution with 5–25% ethyl acetate-hexanes) provided diallyl 2-phthalimidoethylmalonate (451.2 g, 64%) as a colorless oil. $^1$H NMR (300 MHZ, CDCl$_3$) δ 7.82 (m, 2H), 7.72 (m, 2H), 5.85 (m, 2H), 5.30 (m, 2H), 5.22 (m, 2H), 4.60 (m, 4H), 3.80 (t, J=6.6 Hz, 2H), 346 (t, J=7.2 Hz, 1H), 2.30 (dd, J=13.8, 6.9 Hz, 2H). The product of the above-described reaction is illustrated below:

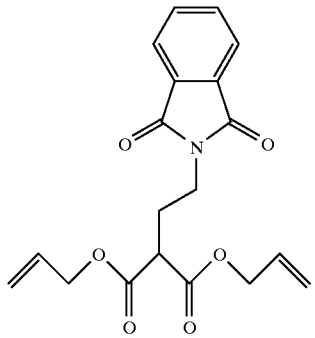

Step 2. A one-necked, 50-mL, round-bottomed flask equipped with a rubber septum and an argon needle inlet was charged with 12 mL THF, trimethylsilyl chloride (0.83 ml, 0.710 g, 6.54 mmol), lithium hexamethyldisilazide (6.50 ml, 1.0 M in THF, 6.50 mmol), and cooled to −78° C. while a solution of 2-dodecanone (1.19 g, 6.46 mmol) in 8.0 ml THF was added dropwise over a period of 30 min via cannula. The resulting mixture was stirred at −78° C. for 30 min. N-bromosuccinimide (1.27 g, 7.13 mmol) was added, and the reaction mixture was stirred at −78° C. for 30 min, diluted with 200 ml of pentane, and washed with three 50 mL portions of brine. The organic phase was dried over $Na_2SO_4$ and concentrated to provide 2.5 g of a yellow solid. Column chromatography on 100 g of silica gel (gradient elution with 3–5% ethyl acetate-hexanes) afforded 0.680 g (40%) of the bromomethyl ketone as a white solid. TLC (5% ethyl acetate-hexanes) R$_f$=0.4. The product of the above-described reaction is illustrated below:

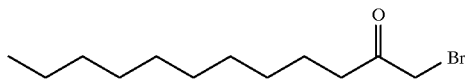

Step 3. A one-necked, 25-ml, round-bottomed flask equipped with a rubber septum and an argon needle inlet was charged with 3 ml of THF and the product of step 1 (314 mg, 0.978 mmol). The resulting mixture was cooled to 0° C. and sodium t-butoxide (88.0 mg, 97% pure, 0.888 mmol) was added. After 30 min, a solution of the product of step 2 (250 mg, 0.950 mmol) in 3 ml of THF was added dropwise via syringe. The resulting mixture was allowed to warm to room temperature and stirred for 16 h. The reaction mixture was diluted with 100 ml of $CH_2Cl_2$ and washed with three 30 ml portions of brine. The organic layer was dried over $MgSO_4$ and concentrated. Column chromatography on 40 g silica gel (gradient elution with 10–30% ethyl acetate-hexanes) afforded 0.300 g (63%) of the desired product as a white solid. TLC (30% ethyl acetate-hexanes) Rf=0.5. The product of the above-described reaction is illustrated below:

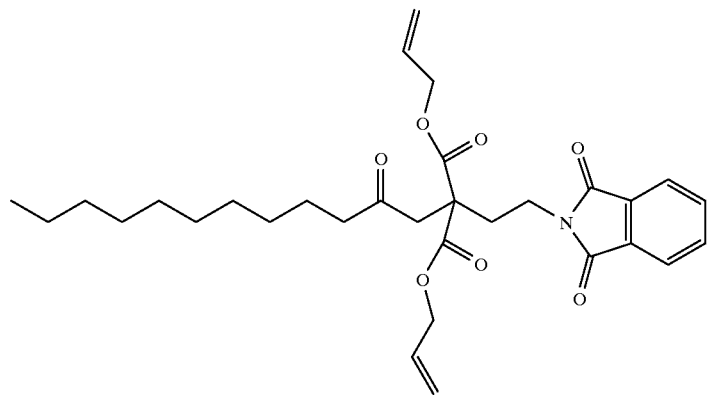

Step 4 Preparation of Example 1. A one-necked, 154-mL, round-bottomed flask equipped with a rubber septum and an argon needle inlet was charged with 2 mL of dioxane, the product of step 3 (300 mg, 0.556 mmol), pyrrolidine (0.12 ml, 0.102 g, 1.44 mmol), and tetrakis(triphenylphospine) palladium (10.0 mg, 0.0086 mmol). The resulting mixture was exposed to a slight vacuum to degas the solution and argon was reintroduced. The reaction mixture was stirred at room temperature for 12 h, the dioxane and pyrrolidine were removed in vacuo, and the residue was redissolved in 2 ml dioxane. The resulting mixture was exposed to a slight vacuum to degas the solution and argon was reintroduced. The reaction mixture was heated at 115° C. for 4 h, 85° C. for 12 h, and concentrated. Column chromatography on 10 g of silica gel (30% ethyl acetate-hexanes with 0.5% acetic acid) afforded 0.137 g (59%) of Example 1 as a white solid (MP 89–90° C.). The product of the above-described reaction is illustrated below:

excess 4 M HCl (soln. in 1,4-dioxane) was added and the mixture was warmed to room temperature and stirred overnite. The solution was concentrated under reduced pressure, diluted with ethyl acetate and successively washed with water, satd. aq. $NaHCO_3$ and satd. aq. NaCl. The organic phase was dried over $MgSO$ filtered and concentrated. Purification by MPLC (5–25% EtOAc-hexanes) provided the target compound (2.45 g, 70%) as a colorless oil. TLC: Rf 0.45 (silica, 15% ethyl actate-hexane). The resulting compound is illustrated below:

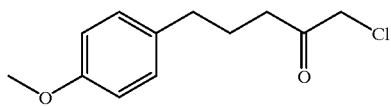

Step 2. A solution of sodium hydride (6.35 g, 264 mmol) in THF (500 mL) was treated with diethyl malonate (47.35 mL,

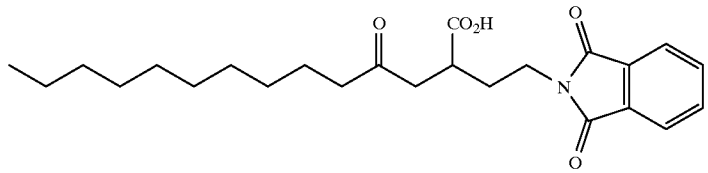

The above methods for the preparation of Example 1 were used to prepare the following examples (TABLE I) using the appropriate bromoketones in step 3.

TABLE I

| Compound | R | Isomer | m.p. (° C.) |
|---|---|---|---|
| I | $C_{10}H_{21}$ | R,S | 89–90 |
| II | $C_{9}H_{19}$ | R,S | 83–84 |
| III | $C_{11}H_{23}$ | R,S | 90–91 |
| IV | $^{a}C_{12}H_{25}$ | R,S | 93–94 |
| V | $C_{13}H_{27}$ | R,S | 88–89 |
| VI | $C_{14}H_{29}$ | R,S | 96–97 |

$^{a}$Preparation of 1-bromo-2-tetradecanone: A one-necked, 100-mL, round-bottomed flask equipped with a rubber septum and an argon needle inlet was charged with 16 mL $CCl_4$, 1,2-epoxitetradecane (2.0 mL, 1.66 g, 7.82 mmol), polyvinyl pyridine (1.00 g), and bromine (0.20 ml, 0.62 g, 3.88 mmol). The resulting mixture was stirred at room temperature under irradiation of a desk lamp (soft white, 60 W) for 30 min. The reaction mixture was diluted with a 1:1 mixture of hexane:ethyl acetate (150ml), washed with a 50 mL portion of saturated $NaHCO_3$, and washed with a 50 mL portion of brine. The organic layer was dried over $MgSO_4$ and concentrated. Column chromatography on 100 g of silica gel (gradient elution with 5–10% ethyl acetate-hexanes) afforded 0.440 g (39%) of 1-bromo-2-tetradecanone as a white solid. TLC (5% ethyl acetate-hexanes) $R_f$ = 0.4.

Examples 7–9-Preparation of Compounds VII–IX
Step 1. A solution of 4-(4-methoxyphenyl)-butyric acid (3.04 g, 15.4 mmol) in $CH_2Cl_2$ (45 mL) was treated with oxalyl chloride (11.6 mL, 2.0 M soln. in dichloromethane) and DMF (1 drop). The solution was heated to reflux for 2 h, cooled to 0° C. and treated with an excess of diazomethane (ether soln.). After stirring an additional 30 min, 312 mmol). After stirring for 2 h, (2-bromoethyl)benzene (32.8 mL, 240 mmol) was carefully added to the reaction mixture. Following the addition, the solution was heated to a gentle reflux for 16 h, cooled to 0° C. and quenched with 2 N HCl. The resulting solution was concentrated under reduced pressure, diluted with EtOAc and washed with satd. aq. NaCl. The organic layer was dried over $MgSO_4$ and concentrated. Vacuum distillation (1.5 mm Hg) provided the substituted malonate (44.4 g, 71%) as a colorless oil. TLC: Rf 0.52 (silica, 20% ethyl actate-hexane). The resulting compound is illustrated below:

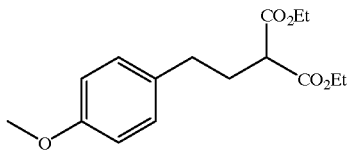

Step 3. A solution of malonate from step 2 (3.50 g, 13.2 mmol) in DME (5 mL) was treated with NaOEt (0.67 g, 9.9 mmol) and stirred for 30 min. While the solution was stirring, a separate flask containing a solution of the α-chloro ketone from step 1 (0.95 g, 4.2 mmol) in DME (5 mL) was treated with LiI (0.62 g, 4.6 mmol), stirred for 15 min, and cannulated into the first solution. After stirring overnite, the reaction mixture was diluted with EtOAc and washed with water and satd. aq. NaCl. The organic layer was dried over $MgSO_4$, filtered and concentrated. Purification by MPLC (5–20% EtOAc-hexanes) provided the desired malonate (0.41 g, 21%) as a colorless oil. TLC: Rf 0.30 (silica, 20% ethyl actate-hexane). The resulting compound is illustrated below:

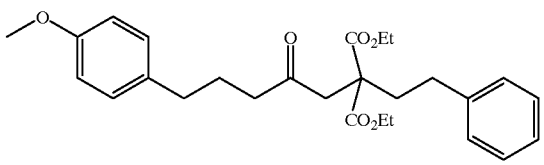

Step 4-Preparation of Example 7. A solution of the diester from step 3 (0.19 g, 0.42 mmol) in ethanol (3 mL) was treated with 2 N NaOH (0.5 mL) and stirred at room temperature. After stirring for 16 h, the soln. was concentrated under reduced pressure, diluted with ethyl acetate, and washed with aq. $K_2CO_3$. The aqueous layer was acidified to pH 1 with 2 N HCl, and extracted with ethyl acetate. The organic layer was dried over $MgSO_4$, filtered and concentrated. The resulting diacid was dissolved in 1,4-dioxane (3 mL) and heated to 65° C. After stirring for 24 h, the soln. was concentrated and purified by flash column chromatography (2–4% $MeOH-CH_2Cl_2$) to give the targeted compound (72.1 mg, 49%). MP 70–71° C. The resulting compound (Example 7) is illustrated below:

The above methods for the preparation of Example VII were used to prepare the following examples (Table II).

TABLE II

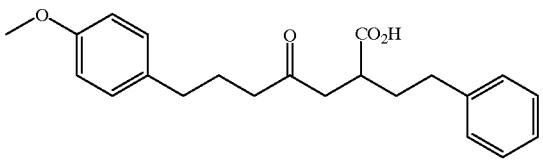

| Compound | n' | isomer | m.p. (° C.)/other characterization |
|---|---|---|---|
| VII | 3 | R,S | 70–71 |
| VIII | 2 | R,S | 75–76 |
| IX | 1 | R,S | $R_f$ 0.45 (silica, 10% $MeOH-CH_2Cl_2$) |

Example 10

Biological Assays of Invention Compounds
P218 Quenched Fluorescence Assay for MMP Inhibition:
The P218 quenched fluorescence assay (Microfluorometric Profiling Assay) is a modification of that originally described by Knight, et al., FEBS Lett. 296 263, 1992 for a related substance and a variety of matrix metalloproteinases (MMPs) in cuvettes. The assay was run with each invention compound and the three MMPs, MMP-3, MMP-9 and MMP-2, analyzed in parallel, adapted as follows for a 96-well microtiter plate and a Hamilton AT® workstation.
P218 Fluorogenic Substrate:
P218 is a synthetic substrate containing a 4-acetyl-7-methoxycoumarin (MCA) group in the N-terminal position and a 3-[2,4-dinitrophenyl]-L-2,3-diaminopropionyl (DPA) group internally. This is a modification of a peptide reported by Knight (1992) that was used as a substrate for matrix metalloproteinases. Once the P218 peptide is cleaved (putative clip site at the Ala-Leu bond), the fluorescence of the MCA group can be detected on a fluorometer with excitation at 328 nm and emission at 393 nm. P218 is currently being produced BACHEM exclusively for Bayer. P218 has the structure:

H-MCA-Pro-Lys-Pro-Leu-Ala-Leu-DPA-Ala-Arg-NH2 (MW 1332.2)

Recombinant Human CHO Stromelysin (MMP-3)
Recombinant Human CHO Pro-MMP-3: Human CHO pro-stromelysin-257 (pro-MMP-3) was expressed and purified as described by Housley, et al., J. Biol. Chem. 268, 4481 (1993).
Activation of Pro-MMP-3: Pro-MMP-3 at 1.72 $\mu$M (100 $\mu$g/mL) in 5 mM Tris at pH 7.5, 5 mM $CaCl_2$, 25 mM NaCl, and 0.005% Brij-35 MMP-3) activation buffer) was activated by incubation with TPCK (N-tosyl-(L)-phenylalanine chloromethyl ketone) trypsin (1: 100 w/w to pro-MMP-3) at 25° C. for 30 min. The reaction was stopped by addition of soybean trypsin inhibitor (SBTI; 5:1 w/w to trypsin concentration). This activation protocol results in the formation of 45 kDa active MMP-3, which still contains the C-terminal portion of the enzyme.
Preparation of Human Recombinant Pro-Gelatinase A (MMP-2):
Recombinant Human Pro-MMP-2: Human pro-gelatinase A (pro-MMP-2) was prepared using a vaccinia expression system according to the method of Fridman, et al., J. Biol. Chem. 267, 15398 (1992).
Activation of Pro-MMP-2: Pro-MMP-2 at 252 mg/mL was diluted 1:5 to a final concentration of 50 $\mu$g/mL solution in 25 mM Tris at pH 7.5, 5 mM $CaCl_2$, 150 mM NaCl, and 0.005% Brij-35 (MMP-2 activation buffer). p-Aminophenylmercuric acetate (APMA) was prepared in 10 mM (3.5 mg/mL) in 0.05 NaOH. The APMA solution was added at $^1/_{20}$ the reaction volume for a final AMPA concentration of 0.5 mM, and the enzyme was incubated at 37° C. for 30 min. Activated MMP-2 (15 mL) was dialyzed twice vs. 2 L of MMP-2 activation buffer (dialysis membranes were pre-treated with a solution consisting of 0.1% BSA in MMP-2 activation buffer for 1 min. followed by extensive $H_2O$ washing). The enzyme was concentrated on Centricon concentrators (concentrators were also pre-treated with a solution consisting of 0.1% BSA in MMP-2 activation buffer for 1 min.. followed by washing with $H_2O$, then MMP-2 activation buffer) with re-dilution followed by re-concentration repeated twice. The enzyme was diluted to 7.5 mL (0.5 times the original volume) with MMP-2 activation buffer.
Preparation of Human Recombinant Pro-Gelatinase B (MMP-9):
Recombinant Human Pro-MMP-9: Human pro-gelatinase B (pro-MMP-9) derived from U937 cDNA as described by Wilhelm, et al. J. Biol. Chem. 264, 17213 (1989) was expressed as the full-length form using a baculovirus protein expression system. The pro-enzyme was purified using methods previously described by Hibbs, et al. J. Biol. Chem. 260, 2493 (1984).
Activation of Pro-MMP-9: Pro-MMP-2 20 $\mu$g/mL in 50 mM Tris at pH 7.4, 10 mM $CaCl_2$, 150 mM NaCl, and 0.005% Brij-35 (MMP-9 activation buffer) was activated by incubation with 0.5 mM p-aminophenylmercuric acetate (APMA) for 3.5 h at 37° C. The enzyme was dialyzed against the same buffer to revmove the APMA.

Instrumentation:

Hamiltion Microlab AT Plus: The MMP-Profiling Assay is performed robotically on a Hamilton MicroLab AT Plus®. The Hamilton is programmed to: (1) serially dilute up to 11 potential inhibitors automatically from a 2.5 mM stock in 100% DMSO; (2) distribute substrate followed by inhibitor into a 96 well Cytofluor plate; and (3) add a single enzyme to the plate with mixing to start the reaction. Subsequent plates for each additional enzyme are prepared automatically by beginning the program at the substrate addition point, remixing the diluted inhibitors and beginning the reaction by addition of enzyme. In this way, all MMP assays were done using the same inhibitor dilutions.

Millipore Cytofluor II. Following incubation, the plate was read on a Cytofluor II fluorometric plate reader with excitation at 340 nM and emission at 395 nM with the gain set at 80.

Buffers:

Microfluorometric Reaction Buffer (MRB): Dilution of test compounds, enzymes, and P218 substrate for the microfluorometric assay were made in microfluorometric reaction buffer consisting of 50 mM 2-(N-morpholino) ethanesulfonic acid (MES) at pH 6.5 with 10 mM $CaCl_2$, 150 mM NaCl, 0.005% Brij-35 and 1% DMSO.

Methods:

MMP Microfluorometric Profiling Assay. The assay is done with a final substrate concentration of 6 $\mu$M P218 and approximately 0.5 to 0.8 nM MMP with variable drug concentrations. The Hamilton is programmed to serially dilute up to 11 compounds from a 2.5 mM stock (100% DMSO) to 10× the final compounds concentrations in the assay. Initially, the instrument delivers various amounts of microfluoromentric reaction buffer (MRB) to a 96 tube rack of 1 ml Marsh dilution tubes. The instrument then picks up 20 $\mu$l of inhibitor (2.5 mM) from the sample rack and mixes it with a buffer in row A of the Marsh rack, resulting in a 50 $\mu$M drug concentration. The inhibitors are then serially diluted to 10, 5, 1, 0.2, 0.05 and 0.01 $\mu$M. Position 1 on the sample rack contains only DMSO for the "enzyme-only" wells in the assay, which results in no inhibitor in column 1, rows A through H. The instrument then distributes 107 $\mu$l of P218 substrate (8.2 $\mu$M in MRB) to a single 96 well cytofluor microtiter plate. The instrument re-mixes and loads 14.5 $\mu$l of diluted compound from rows A to G in the Marsh rack to corresponding rows in the microtiter plate. (Row H represents the "background" row and 39.5 $\mu$l of MRB is delivered in placed of drug or enzyme). The reaction is started by adding 25 $\mu$l of the appropriate enzyme (at 5.86 times the final enzyme concentration) from a BSA treated reagent reservoir to each well, excluding Row H, the "background" row. (The enzyme reservoir is pretreated with 1% BSA in 50 mM Tris, pH 7.5 containing 150 mM NaCl for 1 hour at room temp., followed by extensive $H_2O$ washing and drying at room temp.).

After addition and mixing of the enzyme, the plate is covered and incubated for 25 min. at 37° C. Additional enzymes are tested in the same manner by beginning the Hamilton program with the distribution of P218 substrate to the microtiter plate, followed by re-mixing and distribution of the drug from the same Marsh rack to the microtiter plate. The second (or third, etc.) MMP to be tested is then distributed from a reagent rack to the microtiter plate with mixing, prior to covering and incubation. This is repeated for all additional MMP's to be tested.

IC50 Determination in Microfluorometric Assay: Data generated on the Cytofluor II is copied from an exported ".CSV" file to a master Excel spreadsheet. Data from several different MMPs (one 96 well plate per MMP) were calculated simultaneously. The percent inhibition is determination for each drug concentration by comparing the amount of hydrolysis (fluorescence units generated over 25 minutes of hydrolysis) of wells containing compound with the "enzyme only" wells in column 1. Following subtraction of the background the percent inhibition was calculated as:

((Control values−Treated values)/Control values)×100

Percent inhibitions were determined for inhibitor concentrations of 5, 1, 0.5, 0.1, 0.02, 0.005 and, 0.001 $\mu$M of drug. Linear regression analysis of percnet inhibition versus log inhibitor concentration was used to obtain $IC_{50}$ values.

Profiling Assay Data for Invention Compounds.

All $IC_{50}$ values are expressed as nM. When "I=x%" is shown, x represents the % inhibition at 5 $\mu$M.

TABLE III

| COMPOUND | MMP-3 Fluorogenic $IC_{50}$ | MMP-9 Fluorogenic $IC_{50}$ | MMP-2 Fluorogenic $IC_{50}$ |
| --- | --- | --- | --- |
| I | 4800 | 120 | 1300 |
| II | 5000 | 240 | 1850 |
| III | 2950 | 91 | 750 |
| IV | 2380 | 155 | 515 |
| V | 3384 | 150 | 1100 |
| VI | I = 45% | 235 | 1020 |
| VII | I = 3% |  | I = 18% |
| VIII | I = 13% |  | I = 15% |
| IX | I = 9% |  | I = 18% |

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A matrix metalloprotease-inhibiting compound having the generalized formula:

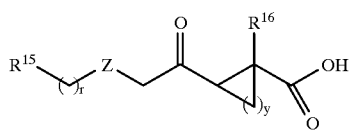

wherein y is 0, 2, or, 3, r is 0–6, Z is $(CH_2)_7$ or $(CH_2)_e$—$C_6H_4$—$(CH_2)_f$, wherein e is 0–1 and f is 1–6; $R^{15}$ is —H, —Cl, —OMe or

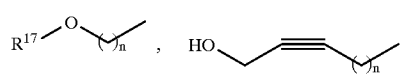

wherein n is 0–4, $R^{17}$ is $C_2H_5$, allyl, benzyl, and $R^{16}$ is

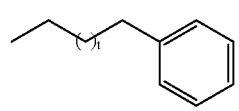

-continued

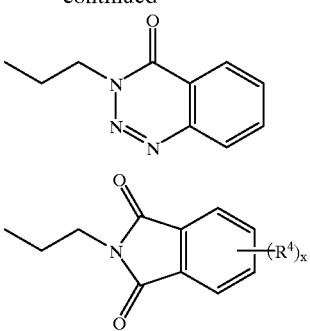

wherein t is 0–2, x is 0–4, and $R^4$ is one of the following: halide, alkyl of 1–6 carbons, OR, $NR_2$, $NO_2$ (R=H or alkyl of 1–6 carbons).

2. A method of inhibiting matrix metalloprotease activity comprising providing an effective matrix metalloprotease-inhibiting amount of a compound according to claim 1.

3. A matrix metalloprotease inhibiting composition comprising a compound according to claim 1 and a pharmaceutically acceptable carrier.

4. A method of treating a mammal comprising administering to the mammal a matrix metalloprotease inhibiting amount of a compound according to claim 1 sufficient to:

(a) alleviate the effects of osteoarthritis, rheumatoid arthritis, septic arthritis, periodontal disease, corneal ulceration, proteinuria, aneurysmal aortic disease, dystrophobic epidermolysis, bullosa, conditions leading to inflammatory responses, osteopenias mediated by MMP activity, tempero mandibular joint disease, demyelating diseases of the nervous system;

(b) retard tumor metastasis or degenerative cartilage loss following traumatic joint injury;

(c) reduce coronary thrombosis from athrosclerotic plaque rupture; or (d) effect birth control.

5. The method of claim 4 wherein said mammal is a human.

6. The method of claim 4 wherein the effect is alleviation of osteoarthritis.

7. The method of claim 4 wherein the effect is retardation of tumor metastasis.

* * * * *